United States Patent
Strauss et al.

(10) Patent No.: US 6,527,732 B1
(45) Date of Patent: Mar. 4, 2003

(54) TORSIONALLY COMPENSATED GUIDEWIRE

(75) Inventors: Brian M. Strauss, Trabuco Canyon, CA (US); Amanda M. Conner, Rancho Santa Margarita, CA (US); Nelson Peralta, Rancho Santa Margarita, CA (US)

(73) Assignee: Micro Therapeutics, Inc., Irvine, CA (US)

( * ) Notice: Subject to any disclaimer, the term of this patent is extended or adjusted under 35 U.S.C. 154(b) by 0 days.

(21) Appl. No.: 09/690,914

(22) Filed: Oct. 17, 2000

(51) Int. Cl.⁷ ................................................. A61B 5/00
(52) U.S. Cl. ...................................... 600/585; 604/523
(58) Field of Search ............................. 600/585, 433, 600/434; 604/523, 533

(56) References Cited

U.S. PATENT DOCUMENTS

| | | | |
|---|---|---|---|
| 4,538,622 A | 9/1985 | Samson et al. | 128/772 |
| 4,545,390 A | 10/1985 | Leary | 128/772 |
| 4,615,198 A | 10/1986 | Hawkins et al. | 72/122 |
| 4,619,274 A | 10/1986 | Morrison | 128/772 |
| 4,811,743 A | 3/1989 | Stevens | 128/772 |
| 4,832,047 A | 5/1989 | Sepetka et al. | 128/772 |
| 4,846,174 A | 7/1989 | Willard et al. | 128/344 |
| 4,846,186 A | 7/1989 | Box et al. | 128/657 |
| 4,854,330 A | 8/1989 | Evans, III et al. | 128/772 |
| 4,884,579 A | 12/1989 | Engelson | 128/772 |
| RE33,166 E | 2/1990 | Samson | 606/194 |
| 4,906,241 A | 3/1990 | Noddin et al. | 606/194 |
| 4,957,110 A | 9/1990 | Vogel et al. | 128/642 |
| 4,971,490 A | 11/1990 | Hawkins | 128/772 |
| 5,011,490 A | 4/1991 | Fischell et al. | 606/159 |
| 5,054,501 A | 10/1991 | Chuttani et al. | 128/772 |
| 5,184,621 A | 2/1993 | Vogel et al. | 128/642 |
| 5,246,009 A | 9/1993 | Adams | 128/772 |
| 5,265,622 A | 11/1993 | Barbere | 128/772 |
| 5,313,967 A | 5/1994 | Lieber et al. | 128/772 |
| 5,328,467 A | 7/1994 | Edwards et al. | 604/95 |
| 5,334,208 A | 8/1994 | Soehendra et al. | 606/108 |
| 5,341,818 A | 8/1994 | Abrams et al. | 128/772 |
| 5,365,942 A | 11/1994 | Shank | 128/772 |
| 5,368,035 A | 11/1994 | Hamm et al. | 128/662 |
| 5,429,604 A | 7/1995 | Hammersmark et al. | 604/95 |
| 5,546,918 A | 8/1996 | Hamm et al. | 128/662 |
| 5,556,408 A | 9/1996 | Farhat | 606/180 |
| 5,702,364 A | 12/1997 | Euteneuer et al. | 604/96 |
| 5,772,609 A | 6/1998 | Nguyen et al. | 600/585 |
| 5,897,584 A | 4/1999 | Herman | 607/122 |
| 6,117,071 A | 9/2000 | Ito et al. | 600/168 |

FOREIGN PATENT DOCUMENTS

| | | | |
|---|---|---|---|
| WO | WO 94/10907 | 5/1994 | A61B/6/00 |

*Primary Examiner*—Max F. Hindenburg
*Assistant Examiner*—Pamela Wingood
(74) *Attorney, Agent, or Firm*—Burns, Doane, Swecker & Mathis L.L.P.

(57) ABSTRACT

A guidewire includes a core and a coil in composite cooperation to enable the guidewire to be used within tortuous regions of the vasculature. The core has a proximal region and a distal region. The distal region includes a flattened end and a tang for connecting the core to the coil. The coil has a proximal end, a distal end and a length extending between the proximal end and the distal end. The ratio between the proximal region and the coil diameter is 1.4:1 or greater. The guidewire includes three joints for attaching the coil to the core. A distal joint attaches the distal end of the coil to the flattened end of the core. A proximal joint attaches proximal end of the coil to the core. A medial joint attaches the length of the coil to the tang. The three joints cooperate with the 1.4:1 ratio to improve torque transmission ability of the guidewire to enable the guidewire to steer through vessels with bends of over 90 degrees and with lumen diameters of less than 3 mm.

25 Claims, 3 Drawing Sheets

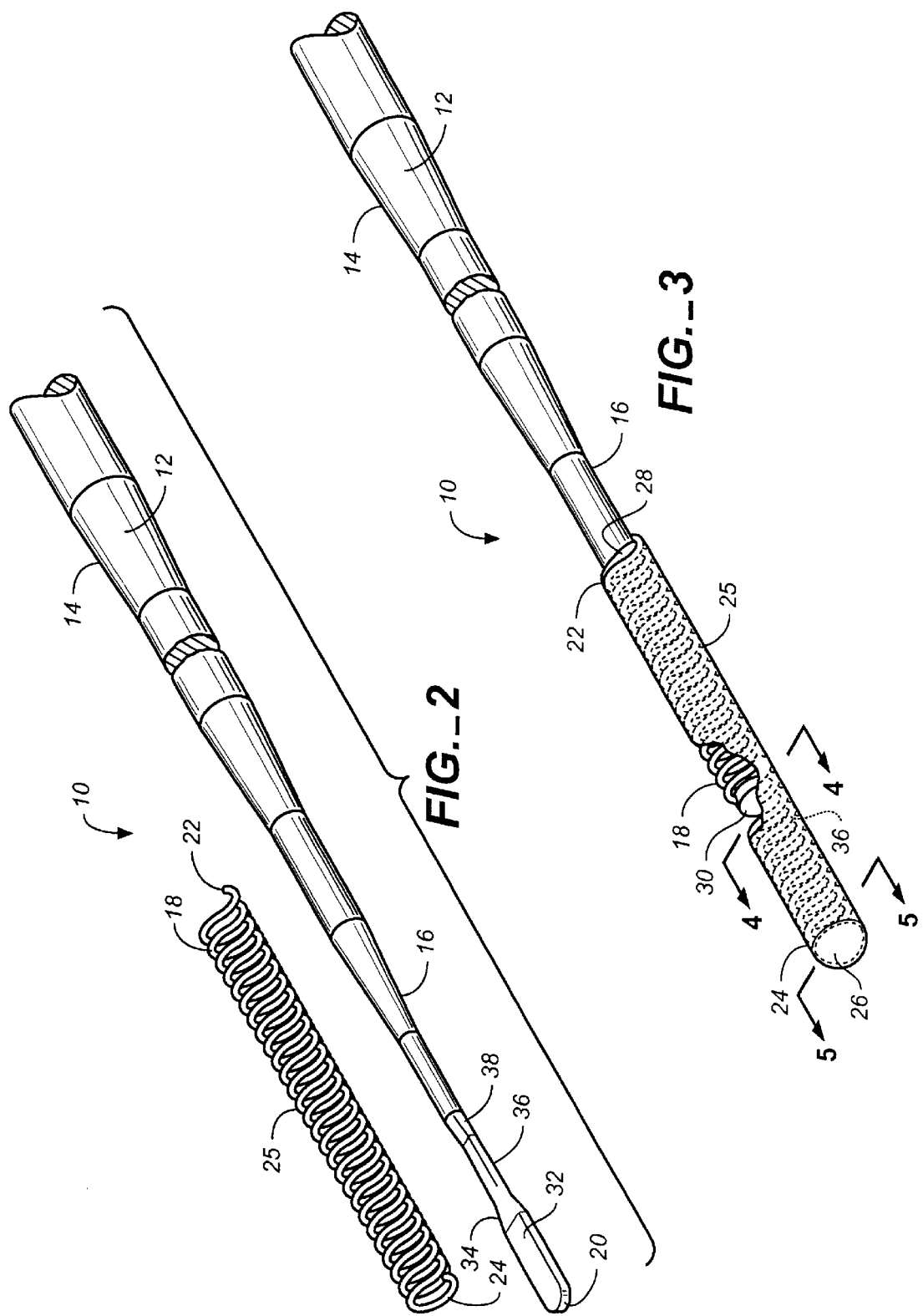

TORSIONALLY COMPENSATED GUIDEWIRE

FIELD OF THE INVENTION

This invention relates to guidewires for intravascular catheters.

BACKGROUND OF THE INVENTION

There is a demand for increasingly smaller diameter guidewires to enable access to the distal reaches of the vascular system, particularly, the neurovascular system. Micro guidewires are those having a distal diameter of 0.010 inches or less. Such guidewires are capable in guiding catheters through much of the vascular system. However, there are limitations to the usefulness of micro guidewires.

One limitation relates to controllability of micro guidewires. Guidewires are typically rotated by twisting the proximal end to steer the distal end through the vasculature. Some of these guidewires have a tip at the distal end with a "J" shape. Rotation of the proximal end of the micro guide wire directs the distal tip to help steer the guidewire through the vasculature.

A micro guidewire having a small diameter will typically have a reduced torsional stiffness compared with guidewires of larger diameter. Rotation of the proximal end of the micro guide wire may not result in rotation of the distal tip when the micro guidewire is in use in a highly tortuous vessel, thus, reducing the ability to steer the distal tip of the micro guidewire to a desired target.

U.S. Pat. No. 5,313,967 to Lieber et al. discloses a guidewire having a helical length for transmitting torque and axial force. The distal tip tapers from the helix and is brazed to the tip spring. While the helical shape of the guidewire is beneficial, the Lieber et al fail to teach how improved torque and axial force transmission can be accomplished in the region of the distal tip.

U.S. Pat. No. 4,846,174 to Willard et al. discloses a guidewire having a flattened distal tip with a uniformly rectangular cross section. The spring has two ends. Each end of the spring attaches to the distal tip.

What is desired is a guidewire having a diameter small enough to access the distal reaches of the vasculature, including the neurovascualture and having sufficient torsional stiffness to enable steering of the guidewire through these tortuous regions. What is also desired is a micro guidewire having a distal end with improved tensile and torsional integrity, yet with the capability to readily bend in any direction.

SUMMARY OF THE INVENTION

A micro guidewire includes a core and a coil in composite cooperation. The core has a proximal region having a minimum outside diameter of 0.012". The distal region includes a flattened end for connecting the core to the coil.

The coil winds about the distal region and has a maximum outside diameter of 0.0085", a proximal end, a distal end and a length extending between the proximal end and the distal end.

Three joints attach the coil to the core. A distal joint attaches the distal end of the coil to the tip of the flattened end. A proximal joint attaches the proximal end of the coil to the core. A medial joint attaches the intermediate portion, i.e. length of the coil to the core. These three joints cooperate to provide improved tensile and torsional integrity to the distal region of the core. Accordingly, the coil and the core form a composite structure.

A discrete portion of the distal region is flattened to form a tang to optimize the torque carrying ability of the distal region. The medial joint forms at the tang, circumscribing the tang to improve the torsional integrity of the distal region of the core. The tang enhances lateral flexibility of the core as compared with a cylindrical section of the same nominal diameter. Furthermore, the tang improves the torsional responsiveness of the distal region. Preferably the tang has a uniform thickness. enabling composite cooperation between the coil and the core near the distal end of the coil. Preferably, the medial joint attaches no more than ⅓ of the length away from the distal end.

According to one aspect of the invention, the preferable ratio of the diameter of the proximal end of the core to the outside diameter of the coil is at least 1.4 to 1. Having a relatively thick proximal end of the core improves the torsional efficiency of the guidewire. In accordance with the present invention, the torsional efficiency achieved is around 80%, or better when the guidewire is in use within a tortuous vessel.

BRIEF DESCRIPTION OF THE DRAWING

FIG. 2 is an exploded perspective view of the guidewire of FIG. 1.

FIG. 3 is a perspective view of the guidewire of FIG. 1.

DESCRIPTION

Figure 1:
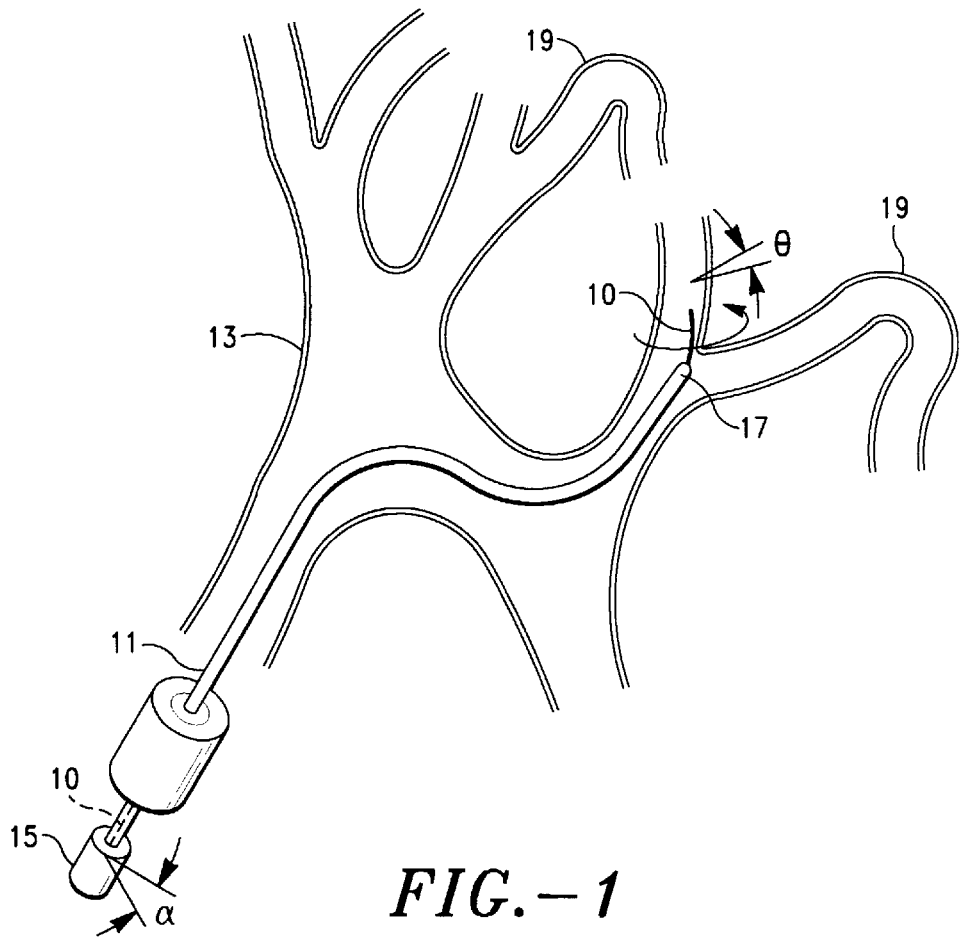
FIG. 1 is a perspective view of a guidewire and catheter in use within a tortuous region of the vasculature of a patient in accordance with the present invention.

FIG. 1 shows a micro catheter 11 disposed within the vasculature 13 of a patient. A guidewire 10 is positioned within the catheter 11 and extends from the distal end 17 of the catheter 11 to guide the catheter 11 through the vasculature 13. The guidewire 10 has two ends.

The micro catheter 11 has an actuator 15. One end of the guidewire 10 extends from the proximal end the catheter 11. The actuator 15 translates and rotate guidewire 10. The other end of the guidewire 10 extends from the distal end 17 of the micro catheter 11.

Rotation of one end of the guidewire 10 through an angle a causes the other end rotates at an angle θ. The angle θ is no less than 80% of the angle α during normal use of the guidewire 10 within highly tortuous regions of the vasculature 13 so that the guidewire 10 achieves at least an 80% torsional efficiency.

For the purposes of this invention, a tortuous path or a tortuous region of the vasculature are defined. A tortuous region of the vasculature has vessels 19 that branch off from more proximal vessels at angles of greater than 90 degrees. The vessels 19 in the distal reaches typically have lumen diameters of 3 mm or less. Typically, a total path length to access tissue in the tortuous region of vasculature is 5 cm or more.

A tortuous path for a guidewire may have some angles of 90 degrees or more to reach the small vessels with lumen diameters of less than about 3 mm. The path will have a typical length of at least about 5 cm.

FIG. 2 and FIG. 3 show the guidewire 10. The guidewire 10 includes a core 12 having a proximal region 14, a distal region 16 and a coil 18 surrounding a part of the distal region 16. The proximal region 14 is formed having a relatively large diameter compared to the distal region 16. Bolstering the size of the distal region 16 diameter enables the core 12 to achieve a high degree of torsional efficiency between the proximal region 14 and the distal tip.

A target of 80% torsional efficiency is achieved within in a highly tortuous vessel by bolstering the core proximal region 14 with a nominal outside diameter of 0.012" or more. The core distal 16 region has a tip 20. The core has a nominal diameter of 0.0024–0.0018" within 2.2 cm from the tip 20. It can be appreciated that these nominal diameter values are exemplary only to illustrate the relative sizing of the distal and proximal regions of the core. This nominal diameter can be flattened or formed to conform to any of a variety of shapes so that the core may have a squared, oval, rectangular and or round shape. Furthermore, this nominal diameter can be increased, reduced, tapered, stepped, or otherwise modified as various applications require.

The coil 18 is preferably fabricated from a platinum or iridium alloy, has a hydrophilic coating and a uniform outside diameter. According to one aspect of the invention, the coil 18 outside diameter is 0.0085", or less. One possible ratio between the proximal region 14 of the core 12 to the outside diameter of the coil 18 is 0.012 to 0.0085, or 1.446:1. Preferably, the ratio is 1.4:1 or greater.

The coil 18 winds about the distal region 16 of the core. The coil 18 has a proximal end 22, a distal end 24 and a length 25 extending between the proximal end 22 and the distal end 24.

The guidewire 10 includes three joints attaching the core 14 and the coil 18. A distal joint 26 attaches the distal end 24 of the coil 18 to the tip 20 of the core 12. A proximal joint 28 attaches the proximal end 22 of the coil 18 to the core 12. A medial joint 30 attaches the length 25 of the coil 18 to the core 12. These three joints 26, 28 and 30 cause the coil 18 and the core 12 to compositely cooperate. Composite cooperation significantly improves tensile and torsional strength at the distal region 16 of the guidewire 10.

Preferably the joints 26, 28 and 30 are soldered, but can alternatively be adhesively bonded, or braised.

The distal region 16 of the core 12 includes a flattened end 32, a first transition region 34 and a second transition region 38. The core 12 has a tang 36 formed between the transition regions 34 and 38. The tang 36 is flattened, providing two opposing flat surfaces that improve the joining of the core 12 and the coil 18. The tang 36 enhances the torsional strength of the distal region 16.

The transition regions 34 and 38 taper, having relatively rounded shapes. The transition region 34 distances the tang 36 from the flattened end 32. The transition region 38 has a relatively larger nominal diameter than the tang 36 to improve the tensile strength at the joint 30. The transition regions 34 and 38 are rounded to enable the distal region 16 of the core 12 to bend more uniformly in any direction. Optimally, the transition regions 34 and 38 are generally frustum shaped.

According to one aspect of the invention, the transition regions 34 and 38 have relatively rounded cross sections and rounded edges more readily achieve uniform multi-directional bending. Rounded transition regions 34 and 38 facilitate this bending better than would be achieved by a comparable distal region having a uniformly flattened cross section or rectangular cross section. The generally rounded transition regions 34 and 38 also inhibit the tip 20 from whipping when the guidewire 10 rotates.

The flattened end 32 is approximately 1 cm in length to enable the flattened end 32 to bend into a "J" configuration. This facilitates steering the guidewire 10 through the narrow, tortuous regions of the vasculature, including the neurovascular system.

The tang 36 has a length of approximately 1.0 cm. It can be appreciated that the distal region 16 of the core 12 can have multiple tangs 36 and transition regions serially aligned. The dimensions of the tang 36 and the transition regions 34 and 38 can vary. It can be appreciated that the length and configuration of the transition regions 34 and 38 may be relatively longer than the tang 36 and vice versa.

According to one aspect of the invention, the medial joint 30 and the tang 36 are closer to the distal end 24 of the coil 18 than the proximal end 22 of the coil 18. Preferably, the medial joint 30 attaches the length 25 to the tang 36 at no more than ⅓ of the length away from the distal end 24 to optimize torsional integrity of the distal region 16 of the core 12.

The tang 36 cooperates with the medial joint 30 to improve the torsional integrity of the distal region 16 of the core 12. The tang 36 is formed from a portion of the core distal region 16, which is flattened to form the tang 36. Accordingly, the tang 36 has a flattened shape. The tang 36 enhances lateral flexibility of the distal region 16 without significantly reducing torsional stiffness of the guidewire 10.

The coil 18 is fabricated from a radiopaque alloy including, for example platinum, iridium and/or tungsten. The guidewire 10 is preferably a micro guidewire for vascular intervention in the neurovascular system. The coil 18 has a length of less than 20 cm and an outside diameter of 0.0085" or less. The core 12 has a length of at least 50 cm, but typically no more than 200 cm.

Figure 4:
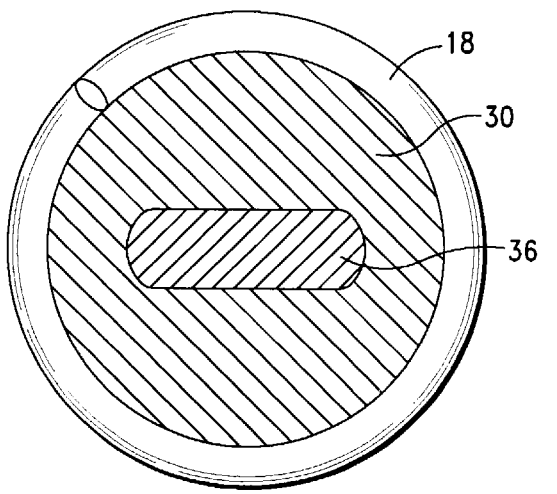
FIG. 4 is a cross-sectional view of an embodiment of the guidewire of FIG. 3 as seen along the line 4—4.

FIG. 4 shows the tang 36 within the coil 18. The medial joint 30 solders the tang 36 to the coil 18. Preferably, the medial joint 30 circumscribes the tang 36, filling the region between the tang 36 and the coil 18, to create a solid annular joining with the coil 18.

Figure 5:
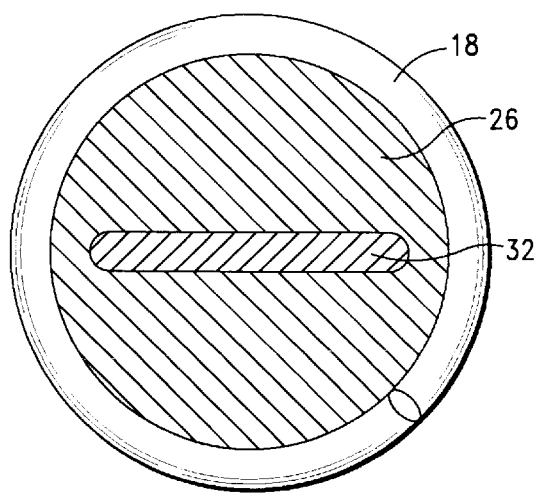
FIG. 5 is a cross-sectional view of an embodiment of the guidewire of FIG. 1 as seen along the line 5—5.

FIG. 5 shows the flattened end 32 of the distal region of the core within the coil 18. The distal joint 26 solders the flattened end 32 within the coil 18. The medial joint (FIG. 3) and the distal joint (FIG. 4) thus cooperate to optimize torsional stiffness of the distal region of the coil and of the guidewire.

Figure 6:
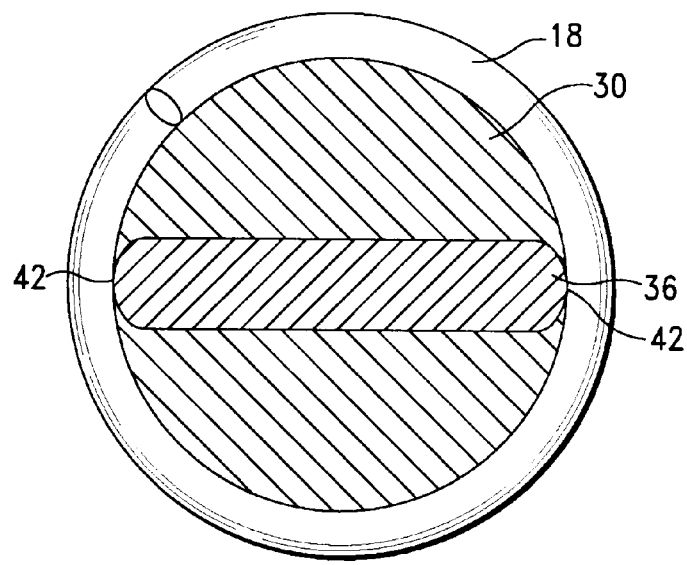
FIG. 6 is a cross-sectional view of an embodiment of the guidewire of FIG. 3 as seen along the line 4—4.

FIG. 6 shows the tang 36 within the coil 18. The tang 36 has two sides 42. The sides 42 contact the coil 18 to optimize the torsional capability of the tang 36 and the area of contact between the tang 36 and the joint 30. Optimizing the area of contact of the joint 30 strengthens the joint 30.

Figure 7:
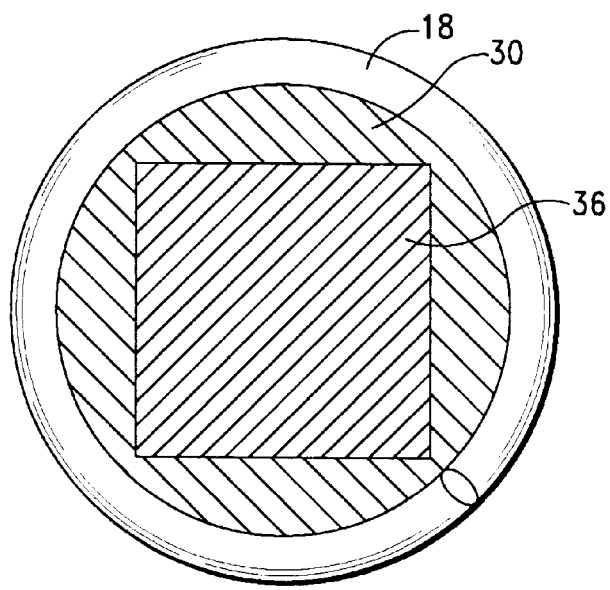
FIG. 7 is a cross-sectional view of an embodiment of the guidewire of FIG. 3 as seen along the line 4—4.

FIG. 7 shows the tang 36 within the coil 18. The tang 36 has a squared cross section to optimize the torsional capability of the tang 36 and the area of contact between the tang 36 and the joint 30. Optimizing the area of contact of the joint 30 strengthens the joint 30.

The present invention is described in terms of a preferred embodiment, however, it can be appreciated that the present invention can be modified to achieve various goals. For example, the ratio of the outside diameter of the proximal region of the core and the coil outside diameter can be increased. Further, the shape of the tang and the flattened end of the core can be modified. The relative position of the medial joint can also change. Accordingly, the present invention is to be limited only by the following claims:

What is claimed is:

1. A guidewire for use in tortuous regions of a vasculature, comprising:
    a core having a proximal region having an outside diameter and a distal region;
    a coil attached to the distal region, the coil having an outside diameter, a proximal end, a distal end and a length extending between the proximal end and the distal end; and
    the coil and the distal region being sized to fit within tortuous regions of the vasculature;
    whereby, the ratio of the core proximal region outside diameter to the coil outside diameter is at least 1.4 to 1 to optimize torsional efficiency of the guidewire when the guidewire is used within the tortuous regions of the vasculature.

2. A guidewire as set forth in claim 1, wherein the core has a proximal region having a minimum outside diameter of 0.012".

3. A guidewire as set forth in claim 2, wherein the coil has an outside diameter of 0.0085" or less to enable the guidewire to steer the coil within a vessel having a lumen diameter of less than 3 mm and bends of greater than 90 degrees.

4. A guidewire as set forth in claim 3, wherein the distal region includes a flattened end and a tang, the guidewire includes a distal joint for attaching the distal end of the coil to the flattened end of the core, a proximal joint for attaching the proximal end of the coil to the core, and a medial joint for attaching the length of the coil to the tang, wherein the medial joint is a solder joint that circumscribes the tang to create an annular joining of the tang and the coil.

5. A guidewire as set forth in claim 4, wherein the medial joint is positioned relatively closer to the distal end than to the proximal end of the coil to optimize torsional integrity of the distal region of the core.

6. A guidewire as set forth in claim 4, wherein the medial joint attaches the length to the core in a position relatively no more than ⅓ of the length away from the distal end to optimize the torsional integrity of the distal region of the core.

7. A guidewire as set forth in claim 3, wherein the coil includes a hydrophilic coating.

8. A guidewire as set forth in claim 3, wherein the coil is fabricated from a radiopaque alloy selected from the group consisting of: platinum, iridium and tungsten.

9. A guidewire as set forth in claim 4, wherein the tang is distanced from the flattened end of the core.

10. A guidewire as set forth in claim 4, wherein the tang is flattened and contacts the coil.

11. A guidewire as set forth in claim 4, wherein the tang has a square cross section.

12. A micro guidewire, comprising:
    a core having a proximal region having an outside diameter of greater than 0.012", and a distal region;
    the distal region includes a flattened end and a tang;
    a coil wound about the distal region, the coil having an outside diameter of 0.0085" or less, a proximal end, a distal end and a length extending between the proximal end and the distal end;
    a distal joint for attaching the distal end of the coil to the flattened end of the core, a proximal joint for attaching the proximal end of the coil to the core, and a medial joint for attaching the length of the coil to the tang; and
    the medial joint attaches the coil to the core in a position relatively no more than ⅓ of the length away from the distal end to optimize torsional stiffness of the distal region of the core.

13. A micro guidewire as set forth in claim 12, wherein the medial joint is soldered and circumscribes the tang.

14. A micro guidewire as set forth in claim 12, wherein the tang is flattened.

15. A micro guidewire as set forth in claim 12, wherein the tang has a uniform thickness.

16. A micro guidewire as set forth in claim 12, wherein the tang has a squared cross section.

17. A micro guidewire as set forth in claim 12, wherein the tang has sides, the sides contact the coil.

18. A method of inserting a guidewire into tortuous regions of the vasculature of a patient, comprising:
    providing a guidewire having a core having a proximal region with an outside diameter and a distal region, the distal region includes a flattened end and a tang; the guidewire includes a coil, the coil has a proximal end, an outside diameter, a distal end and a length extending between the proximal end and the distal end; the ratio of the core proximal region outside diameter to the coil outside diameter is at least 1.4 to 1; the coil has a distal joint for attaching the distal end of the coil to the flattened end of the core, a proximal joint for attaching the proximal end of the coil to the core, and a medial joint for attaching the length of the coil to the tang;
    inserting the guidewire into the tortuous regions of the vasculature of a patient; and
    rotating the proximal region of the core to steer the guidewire.

19. The method of claim 18, wherein rotating the proximal region of the core rotates the distal region with at least 80% efficiency.

20. The method of claim 18, further comprising bending the distal region into a "J" shape before inserting the guidewire into the patient.

21. The method of claim 18, further comprising inserting a catheter into the tortuous regions of the vasculature of a patient and guiding the catheter with the guidewire.

22. A method of inserting a guidewire into tortuous regions of the vasculature of a patient, comprising:
    providing a guidewire having a core having a proximal region with an outside diameter and a distal region, a coil having an outside diameter and being attached to the distal region, the ratio of the core proximal region outside diameter to the coil outside diameter is at least 1.4 to 1 to enable the guidewire to transmit torque from the proximal region to the distal region with an 80% torsional efficiency within a tortuous region of the vasculature;
    inserting the guidewire into a vessel within the tortuous regions of the vasculature of a patient, the vessel having a lumen diameter of less than 3 mm; and
    rotating the proximal region of the core to steer the guidewire.

23. A method as set forth in claim 22, wherein the step of inserting the guidewire includes inserting the guidewire into a vessel having a greater than 90 degree bend.

24. A method as set forth in claim 23 further comprising bending the guidewire at least 90 degrees and steering the guidewire through the vessel with at least 80% efficiency.

25. A method as set forth in claim 23, wherein inserting includes positioning the guidewire within target tissue with a minimum path length of 5 cm.

* * * * *